US008771941B2

(12) United States Patent
Keefe

(10) Patent No.: US 8,771,941 B2
(45) Date of Patent: Jul. 8, 2014

(54) METHODS OF ASSESSING THE RISK OF REPRODUCTIVE FAILURE BY MEASURING TELOMERE LENGTH

(75) Inventor: David L. Keefe, Newport, RI (US)

(73) Assignee: David L. Keefe, New York, NY (US)

(*) Notice: Subject to any disclaimer, the term of this patent is extended or adjusted under 35 U.S.C. 154(b) by 456 days.

(21) Appl. No.: 12/482,176

(22) Filed: Jun. 10, 2009

(65) Prior Publication Data

US 2009/0326316 A1    Dec. 31, 2009

Related U.S. Application Data

(63) Continuation of application No. 10/531,964, filed as application No. PCT/US03/32672 on Oct. 13, 2003, now abandoned.

(60) Provisional application No. 60/419,071, filed on Oct. 16, 2002, provisional application No. 60/452,741, filed on Mar. 7, 2003.

(51) Int. Cl.
*C12Q 1/68* (2006.01)
*A61B 17/425* (2006.01)
*C12N 5/075* (2010.01)
*C07H 21/04* (2006.01)

(52) U.S. Cl.
USPC .............. 435/6.1; 600/33; 435/366; 536/23.1

(58) Field of Classification Search
None
See application file for complete search history.

(56) References Cited

U.S. PATENT DOCUMENTS 5,741,677 A    4/1998    Kozlowski et al.

FOREIGN PATENT DOCUMENTS

WO    03/032672    4/2004

OTHER PUBLICATIONS

Munne, S. et al. Fertility and Sterility 73(6):1209 (Jun. 2000).*
Kinugawa et al., Telomerase Activity in Normal Ovaries and Premature Ovarian Failure. Tohoku J. Exp. Med. 2000, vol. 190, pp. 231-238.
Hultdin et al., "Telomere Analysis by Fluoresense in Situ Hybridization ad Flow Cytometry". Nuc. Acids. Res. 1998, vol. 26, No. 16, pp. 3651-3656.
Liu et al., "Aberrant Fertilization and Early Development of Germ Cells with Dysfunctional Telomeres from Telomerase-Null Mice". Biology of Reproduction. 2002, vol. 66, No. 1, pp. 161-162.
Liu et al., "An Essential Role for Functional Telomeres in Mouse Germ Cells during Fertilization and Early Development". Development Biology. 2002, vol. 249, pp. 74-84.
Allsopp et al., "Telomere length predicts replicative capacity of human fibroblasts", Proc. Natl. Acad. Sci., vol. 89, pp. 10114-10118. (Nov. 1992).
Keefe et al., "Telomere length predicts embryo fragmentation after in vitro fertilization in women—Toward a telomere theory of reproductive aging in women" American Journal of Obstetrics and Gynecology vol. 192, pp. 1256-1261. (2005).
Keefe et al., "Telomeres and reproductive aging", Reproduction, Fertility and Development, vol. 21, pp. 10-14. (2009).
Keefe et al., "The telomere theory of reproductive senescence in women" Curr. Opin. Obstet. Gynecol., vol. 18, pp. 280-285. (2006).

(Continued)

*Primary Examiner* — Diana B Johannsen
(74) *Attorney, Agent, or Firm* — Edwards Wildman Palmer LLP; Richard B. Emmons

(57) ABSTRACT

The invention features a method of identifying oocytes with a risk of reproductive failure and/or aneuploidy based on a telomere length assay.

2 Claims, 2 Drawing Sheets

(56) References Cited

OTHER PUBLICATIONS

Kimura et al., "Offspring's Leukocyte Telomere Length, Paternal Age, and Telomere Elongation in Sperm", PLoS Genetics, vol. 4, Issue 2, pp. 0001-0009. (Feb. 2008).

Liu et al., "Irregular telomeres impair meiotic synapsis and recombination in mice", PNAS, vol. 101, No. 7, pp. 6496-6501.(Apr. 27, 2004).

Liu et al., "Oxidative Stress Contributes to Arsenic-induced Telomere Attrition, Chromosome Instability, and Apoptosis", Journal of Biological Chemistry, vol. 278, No. 34, pp. 31998-32004. (Aug. 22, 2003).

Liu et al., "Requirement of functional telomeres for metaphase chromosome alighnments and integreity of meiotic spindles", EMBO Reports, vol. 3, No. 3, pp. 230-234. (2002).

Navot et al., "Poor oocyte quality rather than implantation failure as a cause of age-related decline in femal fertility", The Lancet, vol. 337, pp. 1375-1377. (Jun. 8, 1991).

Unryn et al., "Paternal age is positively linked to telomere length of children", Aging Cell, vol. 4, pp. 97-101. (2005).

Wright et al., "Telomerase activity in human germline and embryonic tissues and cells." Develop Genet 1996; 18:173-9.

\* cited by examiner

SEQUENCE LISTING

```
<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide used for detecting and
      quantitating telomere length

<400> SEQUENCE: 1
ccctaaccct aaccctaa                                                   18

<210> SEQ ID NO 2
<211> LENGTH: 6
<212> TYPE: DNA
<213> ORGANISM: Artificial Sequence
```

```
<220> FEATURE:
<223> OTHER INFORMATION: Description of Artificial Sequence: Synthetic
      oligonucleotide used for detecting telomere length

<400> SEQUENCE: 2 ttaggg                                                                    6

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide used for detecting telomere length

<400> SEQUENCE: 3 ccctaa                                                                    6

<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide used for detecting telomere length

<400> SEQUENCE: 4 ccccaa                                                                    6

<210> SEQ ID NO 5
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide used for detecting telomere length

<400> SEQUENCE: 5 ccccaaaa                                                                  8

<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide used for detecting telomere length

<400> SEQUENCE: 6 cccaca                                                                    6

<210> SEQ ID NO 7
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide used for detecting telomere length

<400> SEQUENCE: 7 ccctaaa                                                                   7

<210> SEQ ID NO 8
<211> LENGTH: 5
<212> TYPE: DNA
<213> ORGANISM: Artificial Sequence
```

```
<220> FEATURE:
<223> OTHER INFORMATION: Description of Artificial Sequence: Synthetic
      oligonucleotide used for detecting telomere length

<400> SEQUENCE: 8 cccct                                                                        5

<210> SEQ ID NO 9
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide used for detecting telomere length

<400> SEQUENCE: 9 ccctaa                                                                       6

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide used for detecting telomere length

<400> SEQUENCE: 10
ccctaaccct aaccctaa                                                         18
```

METHODS OF ASSESSING THE RISK OF REPRODUCTIVE FAILURE BY MEASURING TELOMERE LENGTH

RELATED APPLICATIONS

This application is a continuation pursuant to 35 U.S.C. § 120 of U.S. Pat. Application Serial No. 10/531,964, filed Dec. 7, 2005, now abandoned which is the national phase application, pursuant to 35 U.S.C. §371, of PCT International Application Serial No. PCT/US2003/032672, filed Oct. 13, 2003, designating the United States and published in English on Apr. 29, 2004 as publication WO 2004/035597 A1, which claims the benefit of U.S. Provisional Patent Application Ser. No. 60/419,071, filed Oct. 16, 2002 and U.S. Provisional Patent Application Ser No. 60/452,741, filed Mar. 7, 2003. The entire contents of these patent applications are incorporated herein by reference.

BACKGROUND OF THE INVENTION

Telomeres are repeated sequences of DNA that cap the ends of chromosomes and prevent the formation of end-to-end fusions. During normal DNA replication, the ends of chromosomes, or telomeres, are left unreplicated. This results in the loss of a small amount of DNA from each chromosome with every cell cycle. This loss is subsequently corrected by an enzyme known as telomerase. Telomerase is a cellular enzyme, which is directed to the nucleotide polymerization or maintenance of telomeres, and contains a complex of protein components and an integral RNA component.

Vertebrate telomeres consist of tandem repeats of the sequence TTAGGG and associated proteins, which cap the ends of chromosomes and protect them from degradation and fusion (Blackburn E. H., *Cell* 106: 661-673, *Nature* 408(6808): 53-6. 2001). Extensive evidence has shown that telomere shortening and dysfunction in cultured somatic cells leads to so-called replicative senescence (Blackburn E. H., *Nature* 408(6808): 53-6, 2000). In turn, reversal of telomere shortening by forced expression of telomerase rescues cells from senescence and extends cell life span indefinitely (Bodnar, A. G., M. Ouellette, et al., *Science* 279(5349): 349-52, 1998). (Vaziri and Benchimol et al., *Curr Biol* 8(5): 279-82. 1998).

Telomeres cap and protect the ends of chromosomes, establish homologue pairing and enhance chiasmata formation during early meiosis, and shorten with cell division and exposure to reactive oxygen (ROS) to mediate cellular aging in somatic cells. Germ cells, like stem cells and cancer cells, contain telomerase, a reverse transcriptase which maintains telomeres by adding telomere repeats to the 3 prime end of DNA, thus allowing germ cells to largely bypass the senescence response exhibited by cells with critically short telomeres. However, telomere elongation is variable and stochastic in most cell types, and in females telomerase activity decreases during late meiosis, so telomere length, determined during early development, provides a developmental bottleneck. Germ cells with adequate telomere length pass across generations, but the fate of eggs "stuck in the bottleneck" by short telomeres is poorly understood.

Active telomerase, composed of a small RNA molecule, known as the telomerase RNA (TR) and of a catalytic subunit, the telomerase reverse transcriptase (TERT), is the primary enzyme for maintaining the length of telomere repeats. Telomerase activity is present during early oogenesis, but is almost absent during late oogenesis and early preimplantation embryo development until the morula stage of development, Thus telomere length in oocytes and early embryos is established during early development. When telomeres reach a critically short length, the cell undergoes cell cycle arrest and apoptosis, so late oogenesis and early preimplantation embryo development may represent a kind of bottleneck for telomere length during development.

The RNA component of the human enzyme contains a short region complementary to the human telomeric repeat sequence (Feng et al. (1995) *Science,* 269:1236). Somatic cells lack telomerase activity, and their telomeres have been found to shorten with cell division both in vivo and in culture. In germ cells and embryos, telomerase actively restores telomeres, so that the chromosomes do not shorten progressively across generations. The short and numerous cell cycles of replicating primordial germ cells and oogonia during oogenesis, however, challenge telomerase to keep up with the progressive telomere shortening. In mature oocytes and early stage preimplantation embryos, telomerase is down regulated until the blastocyst stage of development.

The length of telomeres within the chromosomes of an oocyte at fertilization can determine the resultant telomere length of the embryo. Oocytes exhibit significant variability in telomere length. Oogonia exit mitosis after variable numbers of cell cycles, making the process of telomere shortening stochastic. This inevitable variability in telomere length of chromosomes from oocytes and embryos provides a cytogenetic mechanism to explain the most widely accepted theory of chromosomal aberration or aneuploidy in mammals—the production line hypothesis.

The production line hypothesis states that oogonia exiting from mitosis late during oogenesis have traversed more cell cycles than oogonia exiting from mitosis early during oogenesis. The late exiting oogonia, therefore, have sustained more telomere shortening than their earlier counterparts. The telomeres of oocytes from late-exiting oogonia (late-ovulating oocytes) would be expected to be shorter than those of oocytes from early-exiting oogonia (early-ovulating oocytes).

Female germ cells enter meiosis and arrest at the diplotene stage of prophase I during fetal development and remain arrested at the germinal vesicle (GV) stage for weeks in mice and years in humans until puberty, when the meiotic arrest is lifted in part by gonadotropin stimulation. Pairing and genetic recombination of homologous chromosomes, unique to meiosis, occurs at leptotene/zygotene stages early during the first meiotic prophase, during prenatal life. In fission yeast, plants and mammals, chromosome pairing during leptotene/zygotense is promoted by a process of telomere clustering at the nuclear envelope, called bouquet formation, as chromosomes tethered at their telomeric ends find their homologous partner based on their similar sizes. Bouquet formation is thought to be a prerequisite for pairing and recombination (and therefore chiasmata formation) of homologous chromosomes before meiotic arrest (Bass, Riera-Lizarazu et al., *J Cell Sci,* 113(Pt 6): 1033-42, (2000); de Lange T., *Nature* 392(6678): 753-4 (1998); Scherthan, Jerratsch et al., *Mol Biol Cell* 11(12): 4189-203 (2000); Scherthan, Weich et al., *J Cell Biol.,* 134(5): 1109-25 (1996); Tease C. and Fisher G., *Chromosome Res.* 6(4): 269-76 (1998)). With increasing maternal age in women, meiotic chromosomes increasingly missegregate in human females, leading to aneuploidy, failed implantation, miscarriage, and increased rates of aneuploid offspring (Hassold, T., M. Abruzzo, et al., *Environ. Mol. Mutagen.* 28(3): 167-75 (1996)). Experiments in mice indicate that checkpoints for meiotic chromosome behavior at metaphase-to anaphase transition are less efficient in females compared to males (Hunt, P., R. LeMaire, et al., *Hum Mol*

Genet. 4(11): 2007-12 (1995); LeMaire-Adkins, R., K. Radke, et al., *J. Cell. Biol.* 139(7): 1611-9 (1997)).

$TR^{-/-}$ mice, which are deficient for the telomerase RNA and lack telomerase activity, show progressive telomere shortening with increasing mouse generations, eventually resulting in telomere-exhausted chromosomes and chromosomal end-to-end fusions (Blasco et al. (1997) Cell, 91:25-34; Gonzalez-Suarez et al (2000) *Nat. Genetic.* 26:114-117; Herrera et al. (1999a) *EMBO* 118:1172-1181; Herrera et al (1999b) *EMBO*, 18:2950-2960; Lee et al. (1998) *Nature*, 392:569-574; Rudolph et al. (1999) *Cell*, 96:701-712). Telomerase deficiency in $TR^{-/-}$ mice leads to the disruption of functional meiotic spindles and the misalignment of chromosomes during meiotic division of oocytes in late generation mice. In early generations, however, oocytes from $TR^{-/-}$ mice show no appreciable telomere dysfunction, and exhibit normal chromosome alignment during metaphase (Liu et al. (2002) *Biol. Reprod.* 64:204-210). Telomere dysfunction in late generation $TR^{-/-}$ mice leads to various pathologies including defects in development growth, and immune function, as well as influences tumorigenesis. Female fertility also decreases with increasing $TR^{-/-}$ mouse generations, as evidenced by reduction in litter size, and compromised embryo development, eventually resulting in sterility (Herrera et al, 1999b; Lee et al., 1998).

Oocyte dysfunction is a major source of infertility and failed treatment in infertile women, even when the egg and embryo morphology appear normal. Chromosomal abnormalities are the leading cause of oocyte dysfunction in aging women. Aneuploidy (trisomy and monosomy), or the aberrant segregation of chromosomes during meiosis, is the most commonly identified chromosomal abnormality in humans, observed in at least 35% of first trimester miscarriages, 4% of stillbirths and 0.3% of live-borns (Hassold, et al. (2001) Nat Rev Genet. 2(4):280-91). Recent studies in pre-implantation embryos employing more sensitive technology suggest the presence of even higher rates (up to 80%) of aneuploidies in human eggs (Munne et al. (1999) Hum. Reprod. 14(9):2191-9; Volarcik et al. (1998) Hum Reprod. 13(1): 154-160). Even some young women with multiple failed attempts at in vitro fertilization (IVF) exhibit high rates of aneuploidy in their oocytes and embryos. The clinical consequences of aneuploidy can be catastrophic to both mother and fetus and any attempt to prevent such an occurrence would have profound clinical impact.

Chromosomal aneuploidy is associated with a large number of genetic disorders that could be prevented or prepared for by appropriate diagnosis, e.g., Verp et al. (1990) Chap. 7, in Filkins and Russo, Eds., Human Prenatal Diagnosis, Such disorders include Down's syndrome associated with chromosome 21 trisomy, Edward's syndrome associated with chromosome 18 trisomy, Plateau's syndrome associated with chromosome 13 trisomy, Turner's syndrome associated with an absence of an X chromosome (XO), Keinfelter's syndrome associated with an extra X chromosome (XXY), XYY syndrome, triple X syndrome, and the like.

Some in vitro fertilization (IVF) centers have begun to apply multi probe fluorescent in situ hybridization (FISH) to screen oocytes and embryos for aneuploidy. The application of multi probe FISH analysis for use in human IVF is limited, however, because of the small number of chromosomes which can be studied in a single cell at one time, the diversity of chromosomes susceptible to aneuploidy, and the high rate of mosaics in human pre-implantation embryos.

There is a need for a reliable assay to examine an oocyte's (and the resulting embryo's) predisposition to reproductive failure and/or aneuploidy. Clinical assays that can predict oocyte and embryo developmental potential are needed to help women decide whether to continue infertility treatments which depend on their own eggs or desist and pursue alternatives, such as egg donation or adoption. Such assays would also stave the rising epidemic of multiple gestations associated with assisted reproductive technologies by allowing the transfer of only one or two of the most developmentally competent embryos after IVF. Finally, reliable assays that could predict oocyte and embryo developmental potential would help prevent the creation of babies with debilitating aneuploidies, such as Down's Syndrome.

SUMMARY OF THE INVENTION

The invention is based in part on the application of the quantitative fluorescent in situ hybridization (Q-FISH) assay to measure telomere length in oocytes and polar bodies from women as a means to predict risk of reproductive failure and aneuploidy in embryos and/or offspring, as well as to predict meitotic spindle morphology in oocytes and polar bodies. Meitotic spindle imaging in oocytes is described in published PCT international application WO 02/00013. It has been found that telomere shortening in animals induces not only cytogenic abnormalities but also cell cycle arrest and apoptosis. Aneuploidy can result in cell death and developmental arrest in pre-implantation embryos, as well as a consequent risk of miscarriage and risk of fertility and aneuploidy in any resulting offspring. Accordingly, telomere length can be easily used as an indicator of reproductive failure and/or aneuploidy.

Thus, in one aspect the invention provides a method for determining the risk of reproductive failure in a cell comprising
 obtaining at least one chromosome from the cell;
 measuring telomere length of the chromosome; and
 comparing the measured length of the telomere to the standardized average length of a control telomere; to thereby determine the risk of reproductive failure in the cell.

In a related aspect, the invention provides a method for determining the risk of reproductive failure in an oocyte comprising:
 obtaining at least one chromosome from at least one oocyte in a population of oocytes representative of said oocyte;
 measuring telomere length of the chromosome; and
 comparing the measured length of the telomere to the standardized average length of a control telomere;
to thereby determine the risk of reproductive failure in the oocyte.

In another related aspect, the invention provides a method for determining the risk of reproductive failure in a subject comprising:
 obtaining from said subject at least one chromosome from at least one oocyte in a population of oocytes representative of said oocyte;
 measuring telomere length of the chromosome; and
 comparing the measured length of the telomere to the standardized average length of a control telomere; to thereby determine the subject's risk of reproductive failure.

In yet another related aspect, the invention provides a method for determining the risk of reproductive failure in an oocyte comprising:
 obtaining at least one chromosome from at least one oocyte in a population of oocytes representative of said oocyte;
 hybridizing telomere-specific probes to said chromosome;
 performing quantitative fluorescent in situ hybridization (Q-FISH) analysis;
 measuring telomere length of the chromosome; and
 comparing the measured length of the telomere to the standardized average length of a control telomere;
to thereby determine the risk of reproductive failure in the oocyte.

The invention also provides a method for determining the predisposition of an oocyte to reproductive failure comprising:
  obtaining at least one chromosome from the oocyte;
  measuring telomere length of the chromosome; and
  comparing the measured length of the telomere to the standardized average length of a control telomere;
  to thereby determine the predisposition of the oocyte to reproductive failure, In another aspect, the invention features a method for selecting a fertilized oocyte with a low risk of reproductive failure for in vitro fertilization, comprising:
  obtaining at least one chromosome from the polar body of the fertilized oocyte;
  measuring telomere length of the chromosome; and
  comparing the measured length of the telomere to the standardized average length of a control telomere; to thereby select a fertilized oocyte with a low risk of reproductive failure for in vitro fertilization.

In a related aspect, the invention provides a method of in vitro fertilization comprising:
  selecting a fertilized oocyte by obtaining at least one chromosome from the polar body of the fertilized oocyte;
  measuring telomere length of the chromosome;
  comparing the measured length of the telomere to the standardized average length of a control telomere; and
  implanting the selected fertilized oocyte in the subject.

In yet another related aspect, the invention provides a method for optimizing the viability of an embryo comprising:
  selecting a fertilized oocyte by obtaining at least one chromosome from the polar body of the fertilized oocyte;
  measuring telomere length of the chromosome;
  comparing the measured length of the telomere to the standardized average length of a control telomere; and
  implanting the selected fertilized oocyte in the subject.

The invention also features a method for determining the risk of aneuploidy in a cell comprising:
  obtaining at least one chromosome from the cell;
  measuring telomere length of the chromosome; and
  comparing the measured length of the telomere to the standardized average length of a control telomere;
  to thereby determine the risk of aneuploidy in the cell.

In one aspect, a method for determining the risk of aneuploidy in a cell is provided, comprising:
  obtaining at least one chromosome from at least one cell in a population of cells representative of said cell;
  measuring telomere length of the chromosome; and
  comparing the measured length of the telomere to the standardized average length of a control telomere; to thereby determine the risk of aneuploidy in the cell.

In a related aspect, the invention provides a method for determining the risk of aneuploidy in an oocyte comprising:
  obtaining at least one chromosome from at least one oocyte in a population of oocytes representative of said oocyte;
  measuring telomere length of the chromosome; and
  comparing the measured length of the telomere to the standardized average length of a control telomere;
  to thereby determine the risk of aneuploidy in the cell.

In yet another related aspect, the invention provides a method for determining the risk of aneuploidy in an oocyte comprising:
  obtaining at least one chromosome from at least one oocyte in a population of oocytes representative of said oocyte;
  hybridizing telomere-specific probes to said chromosome;
  performing quantitative fluorescent in situ hybridization (Q-FISH) analysis;
  measuring telomere length of the chromosome; and
  comparing the measured length of the telomere to the standardized average length of a control telomere;
  to thereby determine the risk of aneuploidy in the cell.

The invention also features a method for selecting a fertilized oocyte with a low risk of aneuploidy for in vitro fertilization, comprising:
  obtaining at least one chromosome from the polar body of the fertilized oocyte;
  hybridizing telomere-specific probes to said chromosome;
  performing quantitative fluorescent in situ hybridization (Q-FISH) analysis;
  measuring telomere length of the chromosome; and
  comparing the measured length of the telomere to the standardized average length of a control telomere; to thereby select a cell with a low risk of aneuploidy.

A related aspect of the invention is a method for determining the predisposition of an oocyte to aneuploidy comprising:
  obtaining at least one chromosome from the oocyte;
  measuring telomere length of the chromosome; and
  comparing the measured length of the telomere to the standardized average length of a control telomere;
  to thereby optimize the viability of the embryo.

The invention also features a method of pre-implantation genetic testing to identify an oocyte with a predisposition to aneuploidy comprising:
  obtaining at least one chromosome from the oocyte;
  measuring telomere length of the chromosome; and
  comparing the measured length of the telomere to the standardized average length of a control telomere.

In yet another aspect, the invention provides a kit for determining the risk of reproductive failure and/or aneuploidy in a cell comprising reagents for preparing a chromosomal spread from the cell or at least one cell in a population of cells representative of said cell; labeled telomere-specific repeat probes; reagents for performing quantitative fluorescent in situ hybridization (Q-FISH) analysis on the chromosomal spread; and instructions for measuring the length of a telomere obtained from the chromosomal spread, or obtained from a chromosome of said cell, and comparing the measured length of the telomere to the standardized average length of a control.

DETAILED DESCRIPTION OF THE INVENTION

Definitions

Figure 1:
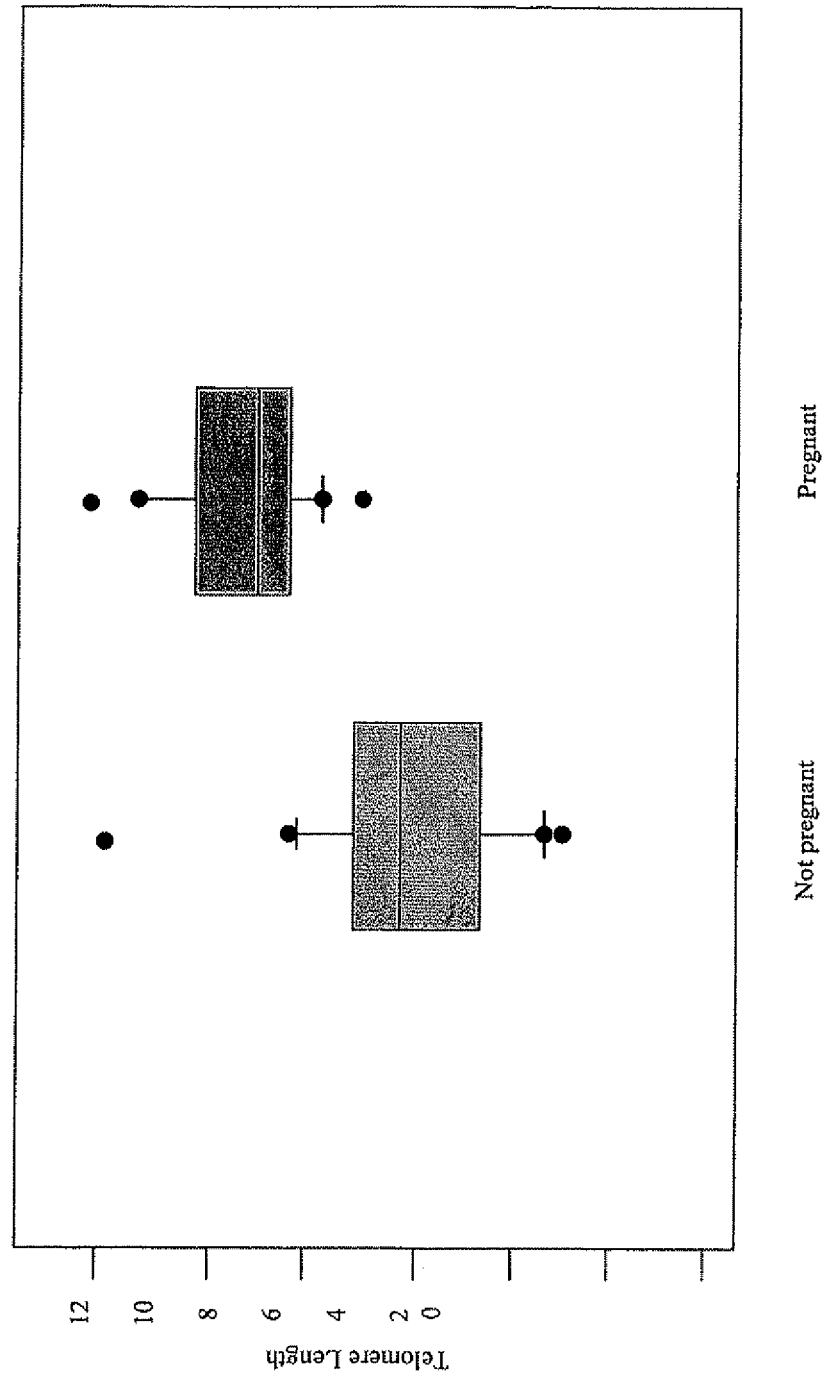
FIG. 1 is a graph showing telomeric lengths from subjects at risk for reproductive failure. Eggs from unsuccessful cycles have shorter telomeres

Before further description of the invention, certain terms employed in the specification, examples and appended claims are, for convenience, collected here.

The term "aneuploidy" is intended to mean a condition wherein a cell contains an abnormal number of chromosomes. The term also encompasses the condition wherein individual genes are present in abnormal quantity, or wherein fragments of individual genes are present in abnormal quantity. An abnormal number of chromosomes is a number greater than or less than the normal diploid number. In humans, aneuploidy is defined as any deviation from the normal human diploid number of 46 chromosomes.

The term "cell" is intended to include any eukaryotic cell, such as a mammalian somatic or germ line cell. The cell of the invention contains DNA, which includes telomeres. In one embodiment, the cell is obtained from a human. In another embodiment, the cell is an oocyte. In yet another embodiment of the invention, a cell is from a population of cells and is representative of the cells in that population. In still another embodiment, the cell of the invention is a somatic cell.

The term "chromosome" is intended to encompass a long structure composed of DNA and associated proteins. Chromosomes consist of nucleic acids. Each animal species has a defined number of chromosomes found in individual cells, referred to as the diploid number. The diploid number refers to the two copies of each homologous chromosome. Egg and sperm cells contain haploid numbers of chromosomes, or one copy of each homologous chromosome. The diploid number is restored at fertilization with the union of the sperm and egg. The term "chromosomal material" is intended to include any number of chromosomes, or portion thereof, taken from an organism. In one embodiment of the invention, chromosomes are from an oocyte. In another embodiment, chromosomes of the invention are from the polar body of a fertilized or unfertilized egg.

The term "embryo" includes any animal in the early stages of growth and development following fertilization up to and including the blastocyst stage. An embryo is characterized as having totipotent cells that are nondifferentiated. In contrast, somatic cells of an individual are cells of the body that are differentiated and not totipotent. A "pre-implantation embryo" refers to a fertilized oocyte with two pronuclei (up to and including a blastocyst), which is not yet implanted in the lining of the female reproductive tract. In general, the pre-implantation embryo contains between about 2 and about 8 cells, although these ranges may vary among species. Typically, the quality assessment for a human or a mouse embryo is performed on an embryo comprising between 2 and 8 cells (i.e., the embryo is assessed between about 18 and about 24 hours post-fertilization).

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as for example, phosphorothioates and thioesters, in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

Homologous nucleic acid sequences, when compared, exhibit significant sequence identity or similarity. The standards for homology in nucleic acids are either measures for homology generally used in the art by sequence comparison or based upon hybridization conditions. The hybridization conditions are described in greater detail below.

As used herein, "substantial homology" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides, Alternatively, substantial homology exists when the segments will hybridize under selective hybridization conditions, to a strand, or its complement, typically using a sequence or fragment derived from any one of SEQ ID NOS; 1 through 10. Typically, selective hybridization will occur when there is at least about 55% homology over a stretch of at least about 14 nucleotides, preferably at least about 65%, more preferably at least about 75%, and most preferably at least about 90%. See Kanehisa (1984) *Nuc. Acids Res.* 12:203-213.

Percent identity and similarity between two sequences (nucleic acid or polypeptide) can be determined using a mathematical algorithm (see, e.g., Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

The term "fluorescent in situ hybridization" or "FISH," as used herein interchangeably, is intended to mean a nucleic acid hybridization technique which employs a fluorophor-labeled probe to specifically hybridize to, and thereby facilitate visualization of, a target nucleic acid. In general, in situ hybridization, including FISH, is useful for determining the distribution of a nucleic acid in a nucleic acid-containing sample such as is contained in, for example, tissues at the single cell level. Such techniques have been used for karyotyping applications, as well as for detecting the presence, absence and/or arrangement of specific genes contained in a cell. FISH involves the use of nucleic acid probes to determine if a particular nucleotide sequence is present in the chromosomal DNA of particular cells. The terms "staining" or "painting" are used interchangeably, and include hybridizing a probe to a chromosome or segment thereof, such that the probe reliably binds to the targeted chromosomal material therein and the bound probe is capable of being visualized. Such methods are well known to those of ordinary skill in the art and are disclosed, for example, in U.S. Pat. No. 5,225,326; U.S. patent application Ser. No. 07/668,751; and PCT WO 94/02646, the entire contents of which are incorporated herein by reference.

The oligonucleotide probe in FISH is labeled with a fluorophor (fluorescent "tag" or "label") according to standard practice. The fluorophor can be directly attached to the probe (i.e., a covalent bond) or indirectly attached thereto (e.g., biotin can be attached to the probe and the fluorophor can be covalently attached to avidin; the biotin-labeled probe and the fluorophor-labeled avidin can form a complex which can function as the fluorophor-labeled probe in the method of the invention). Fluorophors that can be used in accordance with the method of the invention are well known to those of ordinary skill in the art. These include 4,6-diamidino-2-phenylindole (DAPI), fluorescein isothiocyanate (FITC) and rhodamine (see, for example, U.S. Pat. No. 4,373,932, for a list of exemplary fluorophors that can be used in accordance with the methods of the invention). The existence of fluorophors having different excitation and emission spectrums from one another permits the simultaneous visualization of more than one target nucleic acid in a single fixed sample.

The term "hybridization" includes the process by which two complementary nucleic acid molecules anneal to one another. Hybridization is a general technique in which the complementary strands of deoxyribonucleic acid (hereinafter "DNA") molecules, ribonucleic acid (hereinafter "RNA") molecules, and combinations of DNA and RNA are separated into single strands and then allowed to renature or reanneal and reform base-paired double helices. In a preferred embodiment of the invention, in situ hybridization is used which makes possible the detection and localization of specific nucleic acid sequences directly within an intact cell or tissue without any extraction of nucleic acids whatsoever.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11.

The term "in situ hybridization" is intended to mean a nucleic acid hybridization technique which employs a labeled probe to specifically hybridize to and thereby, facilitate visualization of, a target nucleic acid. In situ hybridization is performed by denaturing the target nucleic acid so that it is capable of hybridizing to a complementary probe contained in a hybridization solution. The fixed sample may be concurrently or sequentially contacted with the denaturant and the hybridization solution. Thus, in one embodiment, the fixed sample is contacted with a hybridization solution which contains the denaturant and at least one oligonucleotide probe. The probe has a nucleotide sequence at least substantially complementary to the nucleotide sequence of the target nucleic acid. Optimization of the hybridization conditions for achieving hybridization of a particular probe to a particular target nucleic acid is well within the level of the person of ordinary skill in the art.

Briefly, fluorescence in situ hybridization (FISH) first involves fixing the sample to a solid support and preserving the structural integrity of the components contained therein by contacting the sample with a medium containing at least a precipitating agent and/or a cross-linking agent. Exemplary agents useful for "fixing" the sample are paraformaldehyde, methanol:acetic acid, and Bouin's solution. Alternative fixatives are well known to those of ordinary skill in the art. According to standard practice for performing FISH, the hybridization solution optionally contains one or more of a hybrid stabilizing agent, a buffering agent and a selective membrane pore-forming agent. Following hybridization and subsequent washing, the signal from the fluorescently labeled probe is visualized using imaging techniques well-known to one of ordinary skill in the art.

As used herein, the term "in vitro fertilization" or "IvF" is intended to mean fertilization of an egg with sperm outside of a subject. This procedure is often used as a treatment for infertility. Briefly, eggs are retrieved from a subject and mixed with sperm in a culture dish to allow for fertilization. After a period of incubation, usually two or three days, the newly formed embryos are transferred back to the subject. Examples of conditions for which this technique is used include damaged or absent Fallopian tubes, endometriosis, male factor infertility and unexplained infertility.

The term "labeled" is used herein to indicate that there is some method to visualize the bound probe, whether or not the probe directly carries some modified constituent. "Label" means a chemical used to facilitate identification and/or quantitation of a target substance. Illustrative labels include fluorescent (e.g., FITC or rhodamine), phosphorescent, chemiluminescent, enzymatic, and radioactive labels, as well as chromophores. The term label can also refer to a "tag" that can bind specifically to a labeled molecule. For instance, one can use biotin as a tag and then use avidinylated or streptavidinylated horseradish peroxidase (HRP) to bind to the tag, and then use a chromogenic substrate (e.g., tetramethylbenzamine) to detect and visualize the presence of HRP. In a similar fashion, the tag can be an epitope or antigen (e.g., digoxigenin), and an enzymatically, fluorescently, or radioactively labeled antibody can be used to bind to the tag for visualization purposes. In one embodiment of the invention, the probes are peptide nucleic acid (PNA)-labeled probes, and are labeled according to manufacturer's protocols (Applied Biosystems, Inc., Framingham, Mass.).

The term "oocyte" includes a female germ cell. Oocytes occur in both immature and mature states. "Immature" refers to oocytes that are viable but incapable of fertilization without additional growth or maturation. "Mature" refers to oocytes that have been ovulated from the ova of a female and are capable of being fertilized. Mature also refers to immature oocytes that have been exposed to appropriate hormones or agents to render them capable of fertilization by sperm Oocytes recovered from "unstimulated" follicles or ovaries are natural oocytes obtained from follicles or ovaries that were not treated with any gonadotropins or other hormones or agents to stimulate maturation of the oocytes. Oocytes recovered from "stimulated" ovaries may be either mature or immature. Subjective criteria to estimate the viability and maturity of the ovum can be done microscopically after removal of the ovum from the follicle, and includes assessing the number and density of surrounding granulosa cells, the presence or absence of the germinal vesicle, and/or the presence or absence of the first polar body. In one embodiment of the invention, the oocyte is ovulated from a female subject and obtained for use in IVF. In another embodiment of the invention, the oocyte is immature and is matured in vitro for use in IVF treatment. "Spare" oocytes are those obtained from a female subject for use in IVF procedures but not used for fertilization. Spare oocytes can be obtained from fertile females who are donating their eggs for IVF. In one embodiment of the invention, representative oocytes are chosen from a population of oocytes for the telomere length assay. These representative oocytes may be, for example, spare oocytes.

The term "optimizing the viability of the embryo" is intended to mean maximizing the chance of successful embryonic development. Successful development of the embryo is characterized by the embryo being free of congenital defects. In one embodiment of the invention, the viability of the embryo is optimized by selecting oocytes which are unlikely to exhibit aneuploidy.

As used herein, the term "peptide nucleic acid" or "PNA" means any oligomer, linked polymer or chimeric oligomer, comprising two or more PNA subunits (residues). The term "peptide nucleic acid-labeled" or "PNA-labeled," used interchangeably herein, refers to a probe labeled with a non-naturally occurring polyamide, which can hybridize to a nucleic acid (DNA or RNA) with sequence specificity (U.S.

Pat. No. 5,539,082; Egholm et al. (1993) *Nature* 365:566-568). Examples of uses of PNA-labeled probes include the detection of rRNA in ISH and FISH assays (WO95/32305; WO97/18325), the analysis and detection of mRNA, the analysis and detection of viral nucleic acids, and the analysis and detection of centromeric sequences in human chromosomes and human telomeres (Lansdorp et al. (1996) *Human Mol. Genetics*, 5: 685-691; WO 97/14026). A PNA-labeled probe has also been used to detect human X chromosome specific sequences (WO 97/18325).

The term "predisposition to aneuploidy" is intended to mean that there is a chance that aneuploidy will occur in a cell because conditions are favorable for chromosomal missegregation. In one embodiment, embryos that have a predisposition to aneuploidy are those embryos which develop from an oocyte with telomeres that are abnormal in length. In another embodiment, embryos with a predisposition to aneuploidy are those from oocytes that are produced by females that are likely to produce oocytes with abnormally short telomeres.

The terms "predisposition for reproductive failure" or "risk of reproductive failure" are used interchangeably throughout the specification. The term are intended to mean that the telomeres in the oocytes of a female are shorter than the standard size, resulting in a high probability that the fertilized oocytes will undergo cell cycle arrest shortly after fertilization. The term "reproductive failure" indicates a history of recurrent spontaneous abortion, unexplained infertility or implantation failure following in vitro fertilization and embryo transfer. The term also includes, for example, chromosomal abnormalities, depletion of oocytes, embryonic cell cycle arrest, failure of the embryo to implant, and apoptosis Telomerase activity is present during early oogenesis, but is almost absent during late oogenesis and early preimplantation embryo development until the morula stage of development. Thus telomere length in oocytes and early embryos is established during early development. When telomeres reach a critically short length, the cell undergoes cell cycle arrest and apoptosis, so late oogenesis and early preimplantation embryo development may represent a kind of bottleneck for telomere length during development. In one embodiment, female patients that have a predisposition for reproductive failure are those female patients with oocytes containing chromosomes with telomeres that are abnormal in length. In another embodiment, female patients that have a predisposition for reproductive failure are is identified as having oocytes with abnormally short telomeres.

The term "pre-implantation genetic testing" is intended to mean testing of a certain genetic locus or loci of a cell which is administered prior to implantation of a fertilized oocyte or oocytes by IVF procedures. In one embodiment of the invention, pre-implantation genetic testing is performed on the polar body of a fertilized or unfertilized oocyte. In another embodiment of the invention, pre-implantation genetic testing is performed on an oocyte or oocytes which are representative of a population of oocytes.

The term "probe" includes an oligonucleotide designed to hybridize specifically to a target nucleic acid, wherein the hybridization of the probe to the target can be detected. The probe is labeled as described above so that its binding to the target can be visualized. The probe is produced from a source of the target nucleic acid sequence, for example, a collection of clones or a collection of polymerase chain reaction (PCR) products comprising the target sequence, or portion thereof. Prior to hybridization, the source nucleic acid may be processed in some way, for example, by removal of repetitive sequences or blocking them with unlabeled nucleic add with complementary sequence, so that hybridization with the resulting probe produces staining of sufficient contrast on the target. Telomere-specific staining of the current invention is accomplished by using nucleic acid probes that hybridize to sequences specific to a telomere target. An example of a telomeric probe of the invention is a FITC-labeled peptide nucleic acid (PNA) probe (Applied Biosystems, Framingham, Mass.) comprising the sequence CCCTAACCCTAAC-CCTAA (SEQ ID NO: 1). Other examples of probes that identify telomeres include any one of SEQ ID NOS: 2 through 10.

The term "quantitative fluorescent in situ hybridization" or "Q-FISH" is intended to mean the process by which results from the FISH assay are quantified. In one embodiment of the invention, results from the FISH analysis are analyzed using digital fluorescent microscopes to measure the fluorescent signal from probes directed to telomeric DNA sequences. This analysis is then used to quantify the relative length of a telomeres on a chromosome from a cell. The fluorescent signal from the hybridized probe is indicative of the telomere length of the chromosome. For example, the absence of signal would indicate extremely short or absent telomeres on the chromosomes. A low signal would indicate shortened telomeres, while a medium range signal would indicate an average length telomere. Finally, an intense, strong signal would indicate extra long telomeres relative to the average length.

The term "standardized average length" is intended to mean an average telomere length which is used to determine whether the telomere length of a cell of interest is abnormal. The standardized average length of a cell is determined by measuring the telomere length of a control cell or taking the average telomere length of a population of control cells. In one embodiment of the invention, oocytes which are known to have fertility are used to determine the standardized average length. For example, one or more oocytes obtained from a woman who has demonstrated fertility and who is known to have oocytes which are not predisposed to aneuploidy, can be used to determine the standardized average length of oocytes. In another example, spare eggs and polar bodies obtained from young egg donors, whose eggs generate pregnancies, can be used to determine the standardized average length.

The term "telomere" is intended to mean the modified end of an eukaryotic chromosome which contains repeated sequences of DNA. In humans, telomeres are composed of many kilobases of simple tandem 5'-TTAGGG repeats (Moyzis et al. (1988) *Proc. Natl. Acad. Sci. U.S.A.* 85:6622). During DNA synthesis, the termini of the chromosomes are not fully replicated (Watson (1972) *Nature New Biology* 239: 197,) by the action of DNA polymerase. Incomplete replication occurs at the 3' end of each of the two template strands of the chromosome, because the RNA primer needed to initiate synthesis in effect masks the 3' end of the template The RNA primer is degraded after strand synthesis, and, as there are no additional sequences beyond the 3' end of the template to which primers can anneal, the portion of the template to which the RNA primer hybridized is not replicated. In the absence of other enzymes, the chromosome is thus shortened with every cell division.

The terms "telomeric DNA" or "telomeric region," used herein interchangeably, are intended to mean chromosomal DNA located on the ends of a chromosome. Telomeres consist of a tandem repeat array of a short sequence, which may be desired for experimental manipulation including, e.g., contacting with a probe or primer. For convenience, human telomeric region and human telomeric repeat sequences are typically referred to herein for illustrative purposes. This illustrative use is not intended to limit the invention, and those of skill in the art will recognize that the present methods can be used to measure telomere length of telomeres from any organism.

The term "telomere length" is intended to mean the approximate physical measurement of the length of all telomeric repeat sequences at the end of a chromosome relative to a standardized control. The mean telomere length of a population of cells can provide a standardized average length by which to determine if a telomere is long or short. An abnormal telomere length, as defined herein, is a telomere length which is greater than or less than the standardized average length of a telomere.

The term "telomere length assay" is intended to mean a method by which the ends of chromosomes or telomeres of a cell are measured. Measurement of telomere length in cells can predict risk of aneuploidy. The method of the invention uses a telomere length assay to predict the risk of aneuploidy in oocytes in order to minimize the chance of fertilizing oocytes which may give rise to embryos which will be predisposed to cell cycle arrest and embryo death. For example, telomere length of chromosomes from polar bodies (which contain mirror images of chromosomes still in the oocyte) and/or from spare oocytes, provides an estimate of the risk of aneuploidy in resulting embryos. Likewise, the method of the invention uses a telomere length assay to select oocytes/fertilized oocytes with a low risk of aneuploidy, thereby increasing the likelihood of successful implantation and normal offspring.

In one embodiment of the invention, the telomere length assay is performed using telomeres from chromosomal spreads from unfertilized oocytes and/or polar bodies from fertilized or unfertilized oocytes. In one embodiment of the invention, telomere length is determined using Q-FISH analysis, wherein PNA-labeled telomere repeat probes are hybridized to telomeric DNA in a cell and analyzed by quantitative FISH using digital microscopy and integrated optical density of the fluorescence signal. Digital imaging technology is readily available in any molecular biology laboratory and most IVF centers.

The term "telomere repeats" is intended to mean tandem repeats of a specific nucleotide sequence found within the telomeres at the end of chromosomes. In humans and other vertebrates, the telomere repeats are commonly tandem repeats of the sequence TTAGGG. The number of these tandem repeat sequences, present at the ends of a chromosome, determine the telomere length of a chromosome.

The invention provides methods for determining the risk of reproductive failure and/or aneuploidy in a cell comprising obtaining at least one chromosome from the cell and measuring the telomere length of the chromosome to thereby determine the risk of aneuploidy in the cell. In accordance with the invention, cells include an oocyte, an oocyte representative of a population of oocytes, a polar body form a fertilized oocyte or a polar body from an unfertilized oocyte.

The telomere is preferably detected by a labeled telomere-specific probe which is hybridized to the chromosome prior to measuring telomere length of the chromosome. Preferably, the probe is hybridized to telomere repeats. In one embodiment, the probe is peptide nucleic acid (PNA)-labeled, preferably FITC-labeled (CCCTAA)3 (SEQ ID NO: 10).

In accordance with the invention, the telomere is advantageously measured using quantitative fluorescent in situ hybridization (Q-FISH) analysis, although any other measuring methods know in the art may be used.

In one embodiment of the invention, the oocyte selected is representative of a population of oocytes and a probe is obtained for hybridizing to the chromosome of the oocyte. In one embodiment of the invention, the probe is a labeled telomere-specific probe comprising a nucleic acid sequence identified by any one of SEQ ID NOS: 1-10. In other embodiments, the nucleic acid sequence comprises a sequence having at least about 80 percent sequence identity to any one of SEQ ID. NOS. 1 through 10; more preferably, the nucleic acid sequence comprises a sequence having at least about 90 percent sequence identity to any one of SEQ ID. NOS. 1 through 10; still more preferably the nucleic acid sequence comprises a sequence having at least about 100 percent sequence identity to any one of SEQ ID. NOS. 1 through 10.

In general, the invention provides assays to determine the predisposition of cells, for example, an oocyte to reproductive failure and/or aneuploidy in order to optimize the implantation and viability of the embryo. In another embodiment, the invention provides a method of pre-implantation genetic testing for screening oocytes with a predisposition to aneuploidy. Oocytes which have a predisposition to aneuploidy are more likely to give rise to embryos with developmental defects. The oocytes are screened for use in in vitro fertilization. To optimize the overall success of in vitro fertilization and to maximize the chance of a normal embryo, oocytes with abnormally long or short telomeres are not fertilized and/or implanted in the patient undergoing IVF treatment. In one embodiment, telomere lengths are determined by Q-FISH analysis, using PNA-labeled probe, quantitative digital microscopy, and integrated optical density of the fluorescence signal.

In particular, the invention features a method for distinguishing oocytes which have a predisposition to reproductive failure and/or aneuploidy in order to optimize the viability of an embryo for in vitro fertilization treatment. In order to assay oocytes for their predisposition to aneuploidy, chromosomes are obtained from the oocytes and/or polar bodies to analyze the length of their telomeres. In one embodiment of the invention, an oocyte is selected for the telomere length assay from a population of oocytes. The telomere length of the selected oocyte is representative of the population of oocytes. The representative oocyte can be a spare oocyte which is not intended for use in IVF. In another embodiment, a polar body from a fertilized or unfertilized oocyte is obtained, and its chromosomes are used in the telomere length assay of the invention Polar bodies contain mirror images of chromosomes from the oocyte from which they are obtained. Polar bodies and oocytes are obtained through techniques known to those of ordinary skill in the art of in vitro fertilization procedures.

Based on the teachings of the invention, telomeric DNA from oocytes and/or polar bodies can be used to predict the developmental potential of an embryo based on the correlation between telomere length and a predisposition of the oocyte or polar body to aneuploidy. Standard molecular biology techniques known to one of ordinary skill in the art can be used to determine the length of a telomere, including, for example, quantitative polymerase chain reaction (PCR) (Cawthon (2002) *Nucleic Acids Research*, 30:1-6). In situ techniques can also be used to measure telomere length, including, for example, primed in situ labeling (PRINS) and fluorescent in situ hybridization (FISH) (Therkelsen, et al. (1995) *Cytogenet Cell Genetic.* 68:115-118; Pinkel et al. (1986) *PNAS USA,* 83 :2934-2938). To better quantify telomere length using FISH, quantitative FISH (Q-FISH) can be performed according to standard protocols, and those described herein. Q-FISH analysis is enhanced through the use of PNA-labeled probes, which are commercially available (see DAKO (Denmark), Applied Biosystems (Framingham, Mass.)).

In another embodiment, a female's predisposition to reproductive failure is determined by the length of the telomeric ends of a chromosome. An oocyte is selected for the telomere length assay from a population of oocytes. The telomere length of the selected oocyte is representative of the population of oocytes. The representative oocyte can be a spare oocyte which is not intended for use in IVF. In another embodiment, a polar body from a fertilized or unfertilized oocyte is obtained, and its chromosomes are used in the telomere length assay of the invention.

In one embodiment, telomere length is measured using Q-FISH analysis, which is described below. First, chromosomes are obtained from a cell or cells of interest, and are morphologically preserved. The chromosome sample, or chromosome spread, is prepared according to standard techniques such that individual chromosomes remain substantially intact and typically comprise metaphase spreads or interphase nuclei. Cells described in the methods of the invention include polar bodies and oocytes. Cells can be morphologically preserved by fixation using conventional methods (see for example, A. G. Everson Pearce (1980) *Histochemistry Theoretical Applied*, 4th Ed., Churchill Livingstone, Edinburgh, for details relating to the general techniques for preparing and fixing tissue).

The cells of the invention can be fixed on a support, such as slides or filters. For example, oocytes can be fixed by spinning small volumes of cells onto slides. Chromosomal preparations or the chromosome spread can also be pre-treated on the support. Pretreatments include, but are not limited to, RNAse treatment to remove endogenous RNA, protease treatment to increase the accessibility by digesting protein surrounding the telomeres, and detergent treatment when it is suspected that lipid membrane components have not been extracted by other procedures.

The chromosome spread is then treated with a telomere-specific probe. The probe is a nucleic acid, or analog thereof which is capable of hybridizing to telomeric DNA. Nucleic acid analogs differ from natural DNA in that they do not have a deoxyribose or ribose backbone. In one embodiment of the invention, probes are constructed from the nucleic acid analog called peptide nucleic acid (PNA) which contains a polyamide backbone (described in WO 92/2070). PNA probes have been used in FISH to study telomeres in hematopoietic cells (Lansdorp et al. (1996)), as well as in multicolor FISH experiments detecting telomere sequences (Taneja et al. (2001) *Genes, Chrom., and Cancer* 30:57-63). Other examples of analogs which can be used to make probes include analogs having cyclic backbone moieties comprising furan or morpholine rings, or acyclic backbone moieties (WO 86/05518). Determination of whether a probe hybridizes to a telomeric sequence can be accomplished by hybridizing the probe to a nucleic acid molecule comprising multiple copies of the telomeric repeat sequences using the hybridization media and conditions described herein.

In one embodiment of the invention, the probe for detecting and quantitating the length of a telomere in a chromosome is a PNA-labeled probe having the following sequence: CCCTAACCCTAACCCTAA (SEQ ID NO: 1). In another embodiment, the probe for measuring the length of a telomere contains the repeat sequence TTAGGG (SEQ ID NO: 2), CCCTAA (SEQ ID NO: 3), CCCCAA (SEQ ID NO: 4), CCCCAAAA (SEQ ID NO: 5), CCCACA (SEQ ID NO: 6), CCCTAAA (SEQ ID NO: 7), CCCCT (SEQ ID NO: 8), CCCTAA (SEQ ID NO: 9), or FITC-labeled (CCCTAA)3 (SEQ ID NO: 10).

In another embodiment of the invention, the telomere specific probe comprises a nucleic acid sequence having at least about 80 percent sequence identity to any one of SEQ ID. NOS. 1 through 10; more preferably, at least about 90 percent sequence identity to any one of SEQ ID. NOS. 1 through 10; still more preferably, at least about 100 percent sequence identity to any one of SEQ ID. NOS. 1 through 10.

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The nucleotides at corresponding nucleotide positions are then compared. When a position in the first sequence is occupied by the nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment the percent identity between two nucleotide sequences is determined using the GAP program in the GCG software package (available at online through the Genetics Computer Group), using a NWSgapdna. CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (*Comput Appl. Biosci.* 4:11-17 (1988)) which has been incorporated into the ALIGN program (version 2.0 or version 2.0U), using a PAM120 weight residue table, a gap length penalty of 12 and a gap penalty of 4.

The probe used in the method of the invention is preferably labeled with one or more detectable substances. In a preferred embodiment of the invention, the probe of the invention is labeled with a detectable substance so that formed hybrids can be visualized microscopically after the in situ hybridization procedure. Visualization can be achieved either directly or indirectly depending on the nature of the label used for the probe. Detectable substances which can be used in direct visualization methods of the probe include, but are not limited to, fluorophores, isotopes, and chemiluminescent compounds. Examples of isotopes include iodine $I^{125}$, $I^{131}$ or tritium. Examples of fluorophores which can be used to label the probe of the invention include fluorescein-isothiocyanate (FITC), tetramethyl rhodamine isothiocyanate (TRITC), amino-methyl coumarin acetic acid (AMCA) (Molecular Probes, Eugene, Oreg.), Texas Red (Molecular Probes, Eugene, Oreg.), and carboxymethylindocyano dyes such as Cy2, Cy3, or Cy5 (Biological Detection Systems, Pittsburgh, Pa.). An example of a chemiluminescent material is luminol. The probe of the invention can be labeled with any of these detectable substances using methods conventionally known in the art.

The probe can also be labeled with a detectable substance which is detected in an indirect method. The probe can be labeled with a detectable substance so that formed hybrids are visualized after reacting with an element (e.g., a substrate, an antibody, etc.) which results in a detectable signal. Detectable substances which may be used in indirect methods include enzymes (e.g., horseradish peroxidase, alkaline phophatase, β-galactosidase, or acetylcholinesterase) and haptens (e.g., biotin, digoxigenin). For example, if biotin is used as the detectable substance, in situ hybridized sequences are detected using (strept)avidin or anti-biotin antibodies. The probe may be labeled with enzymes and haptens using conventional methods known in the art, for example, in Pattersen et al. (1993) *Science,* 260:976-979.

The probe of the invention can also be labeled with more than one detectable substance. For example, the probe may be labeled with two or more fluorophores. The probe may also be labeled with substances detectable for both direct and indirect detection methods. The method of the invention can also be practiced using differently labeled probes. For example, the method may use three probes having the same nucleic acid sequence but each labeled with a different detectable substance, such as three different fluorophores.

In another embodiment, the method of the invention is performed using a probe and a counterstain. A counterstain can be used to visualize another feature of the cell (e.g., nucleic acids, cell walls, nuclei, etc.), and includes, for example, DAPI and Hoechst stains. In accordance with the invention, a counterstain can be used to visualize the complete chromosome to compare with the visual signal from the telomere-specific probe.

The detectable substance of the probe may provide a calorimetric, photometric, radiometric, etc. signal which can be detected by a wide variety of means. For example, the method of the invention could employ a suitable detectable device capable of detecting a change in absorption density, a change in fluorescence, or radioactive emission, or a shift in the absorbance of a characteristic $\lambda_{max}$, for example, the $\lambda_{max}$ of the detectable molecule, as detailed in the Examples which follow.

In a one embodiment of the invention, the probe is labeled with a fluorophore such as fluorescein-isothiocyanate (FITC), tetramethyl rhodamine isothiocyanate (TRITC), amino-methyl coumarin acetic acid (AMCA) (Molecular Probes, Eugene, Oreg.), Texas Red (Molecular Probes, Eugene, Oreg.), or carboxylmethylindocyano dyes such as Cy2, Cy3, or Cy5 (Biological Detection Systems, Pittsburgh, Pa.). Images of fluorophore labeled probes hybridized to target telomeric nucleic acid sequences can be created using conventional techniques known in the art (see also Nederlof, et al (1992) *Cytometry* 13:839-845). In a preferred embodiment, the images are formed electronically, and most preferably are digital (discussed further below).

The probe is hybridized to telomeric DNA by incorporating the probe into an appropriate hybridization medium. Generally, hybridization medium has a low ionic strength and typically contains a buffer, denaturing agent and a blocking reagent. Examples of buffers include TRIS and HEPES. Examples of suitable denaturing agents include formamide and DMSO. A blocking reagent is any reagent which substantially blocks non-specific binding of the probe.

The hybridization medium comprising the telomeric-specific probe is applied to the chromosomal DNA. The hybridization probe and the chromosomal DNA are denatured simultaneously by heat or pH treatment. The probe and telomeric DNA are hybridized under stringent conditions.

Following the in situ hybridization process, the image of the hybridized to a detectable probe is captured using imagery equipment standard in a molecular biology or IVF laboratory. In brief, instrumentation needed to create a digital image consists of a microscope system, a detector for collection of images, and computer hardware and software for image analysis.

In one embodiment of the invention, fluorescence microscopy is used to quantitatively analyze the FISH results. For fluorescence microscopy, objective lenses are generally used with high magnification and high numerical aperture, since these characteristics determine the spatial resolution and light collecting properties. For example, a Leitz Dialux epifluorescence microscope equipped with a 100 W mercury-arc lamp and a Neofluor 1,40 NA oil objective can be used to measure fluorescence, and the filter used for selection of the fluorophore may be as follows: PL450-SP490 (excitation filter), DM510 (dichroic mirror), and LP515-SP560 (emission filters). A detector for imaging the FISH results should be selected so that it has sufficient sensitivity to detect the fluorescing signals obtained by FISH, for example, detection of fluorescing signals that can be differentiated from background fluorescence, as detailed in the Examples which follow. Ideally the detector also provides a linear response to a wide range of wavelengths, has a high signal to noise ratio, and has wide dynamic range and little geometric aberrations.

For Q-FISH analysis, the intensity of a spot may be calculated as the integrated intensity of all pixels within the area of the spot corrected for the background. The length of the telomere is quantitated from the specific fluorescent intensity of all the pixels within the area of the spot (telomeric region) corrected for the background. Methods for determining telomere length quantitatively by analyzing FISH results are described in Zijlmans et al. (1997) *PNAS* 94:7423-7428. Digital images are recorded and a computer program is used for image analysis.

In general, computer image analysis is used to optimize signal to noise ratio of telomere fluorescence from human oocytes and polar bodies. Telomeres can be imaged using a number of commercially available computer image analysis programs. An example of a commercially available analysis program is the MetaMorph® Imaging System program (Universal Imaging Corporation (Downingtown, Pa.). Software, which can be programmed to integrate intensity and area of telomere fluorescence, is also available in the public domain; e.g., NIH provides image analysis software at no cost. It will be appreciated that macro programs can also be written for commercially available software, which will further optimize the signal to noise ratio of telomere fluorescence from human oocytes and polar bodies.

Calibration of the Q-FISH technique for telomere length is performed using known telomere lengths, including, for example, genetically engineered artificial telomeres. Genetically engineered artificial telomeres can be generated based on the determined standardized average length, In another example, chromosome spreads from mouse oocytes from strains known to have long and/or short telomeres can also be used to calibrate telomere length. Examples of mouse strains known to have abnormal length telomeres include the $TR^{-/-}$ strain (Blasco, et al. (1997) *Cell* 91:25-34) and the $ATM^{-/-}$ strain (Hande et al. (2001) *Hum. Mol. Genet.* 10:519-528).

Telomeres are quantified as being average, longer, or shorter than the determined standard telomere length of the cell whose telomeres were analyzed, The standard telomere length of a cell can be determined by the results obtained from Q-FISH analysis of a control telomere. Measurement of telomere length is further described in Martens et al. (1998)

*Nature Genetics* 18:76-80. Cells whose chromosomes are determined to have abnormal length telomeres are likely to give rise to aneuploidy. In one embodiment of the invention, an oocyte which is analyzed by Q-FISH and is determined to have abnormal length telomeres, is not used for in vitro due to a predisposition to aneuploidy. An oocyte with a predisposition to aneuploidy is not likely to give rise to a viable embryo, and would not be chosen by a clinician for in vitro fertilization purposes. In another embodiment, a polar body is analyzed by Q-FISH analysis for a predisposition to aneuploidy.

Exemplification

The invention is further illustrated by the following examples which should not be construed as limiting.

EXAMPLES

Materials and Methods

Spare human eggs (N=43) matured from GV stage oocytes in vitro, retrieved for attempted intracytoplasmic sperm injection, were donated by consenting patients (N=24) undergoing ART for infertility. FISH analysis of telomere length and extraction of clinical characteristics and outcomes were performed by separate investigators blinded to each others' findings.

Cumulus cells were removed by pipetting after brief incubation in 0.03% hyaluronidase. GV oocytes were matured in vitro for 24 to 48 hours until they reached MII stage of development.

Analysis of Telomeric Function using Quantitative Fluorescence in Situ Hybridization (Q-FISH) with Telomere Probe Q-FISH has become the method of choice for examination of both telomere length and loss in single cells (Zijlmans, Martens et al. 1997, *PNAS USA*, 94: 7423-7428.) Chromosome spreads were prepared by a hypotonic treatment of oocytes or spermatocytes with 1% sodium citrate for 20 min, followed by fixation in methanol:acetic acid (3:1), and air dried. FISH with FITC-labeled (CCCTAA)3 (SEQ ID NO: 10) peptide nucleic acid (PNA) probe (Applied Biosystems, Framingham, Mass.) was performed according to the manufacturer's protocol. Chromosomes were counter-stained with 0.2 μg/ml Hoechst 33342. Embryos were mounted onto a glass slide in Vectashield mounting medium (Vector Laboratories, Burlingame, Calif.). Telomeres were detected with a FITC filter using a Zeiss fluorescence microscope (Axioplan 2 imaging) and images were captured by an AxioCam using AxioVision 3.0 software.

Quantitative fluorescence in situ hybridization (Q-FISH): Telomere FISH was performed on chromosome spreads from oocytes or polar bodies, as previously described (Hande, Samper et al. 1999, *J. Cell Biol.* 144(4): 589-601). Telomeres were denatured at 80° C. for 3 min and hybridized with FITC-labeled (CCCTAA)3 (SEQ ID NO: 10) peptide nucleic acid (PNA) probe (Applied Biosystems, Framingham, Mass.), washed and mounted in Vectashield mounting medium added with 0.5 μg/ml DAPI. For quantitative measurement of telomere length, telomere fluorescence intensity was integrated using the TFL-TELO program (Poon, Martens et al. 1999, *Cytometry*, 36: 267-278), kindly provided by P. Lansdorp, and calibrated with fluorescence beads. Telomere length (kb) was estimated based on the relative fluorescence intensity, using standard cell lines with known telomere length (McIlrath, Bouffler et al. 2001, *Cancer Res.*, 61(3): 912-5).

Example I

Calculation of Control for Telomere Length Assay

To determine the standardized average length of a telomere against which to compare telomere length in oocytes from women with reproductive problems, telomere length is determined from spare oocytes and polar bodies of control oocytes. Telomere lengths are determined by the number of tandem repeats of a specific nucleotide sequence found within the telomeres at the end of chromosomes. In humans and other vertebrates, the telomere repeats are commonly tandem repeats of the sequence TTAGGG.

Control oocytes and/or polar bodies are obtained from donors undergoing IVF to donate their oocytes to women with egg infertility. For example, oocytes can also be retrieved for control studies from women undergoing intracytoplasmic sperm injection (ICSI) for severe male factor infertility or egg donation. Other factors considered for women donors include having a day three FSH values less than 9 IU/ml, inhibin B levels greater than 45 and estradiol levels less than 80 pg/ml at least 12 eggs retrieved after COH with standard gonadotropin dosing, and no known diagnosis of female infertility. Oocytes are retrieved by transvaginal needle aspiration from the ovary, performed under gentle intravenous sedation after controlled ovarian hyperstimulation (COH), per standard protocols. Methods for obtaining eggs for egg donation are described in Klein, et al. (2002) *Best Pract Res. Clin. Obstet. Gynaecol.* 16:277-291.

Human oocytes are cultured according to standard, published clinical protocols. Protocols for culturing human oocytes can also be found throughout the literature, including, for example, Quinn et al. (1998) *Fertil. Steril.* 69:399-402.

Polar bodies from control oocytes are obtained and used as a control according to whether the oocyte from which they arose went on to form normal babies after the resulting embryos are transferred into the uterus of the recipient women. Polar bodies are biopsied according to standard protocols, as described, for example, in Verlinsky et al. (1996) *J. Assist. Reprod. Genet.* 13(2): 157-162. Briefly, for biopsy of polar bodies, first the egg or oocyte was placed on the holding pipette of a micromanipulator under 40 X objective on an inverted microscope. The zona was broached by laser, acid tyrodes, pronase or mechanical dissection. The polar body was teased out with gentle suction into a biopsy pipette affixed to the second micromanipulator. The polar body was ten released onto a slide where a chromosome spread was made. The first polar body was obtained before fertilization, while the second was obtained after.

Example II

Comparative Telomeric Lengths Between Dysfunctional Oocytes and Normal Oocytes

For comparative purposes, oocytes are also obtained from women who are known to have dysfunctional oocytes. Eggs are retrieved by transvaginal aspiration under light intravenous sedation after controlled ovarian hyperstimulation (COH). Dysfunctional eggs are retrieved from women undergoing ICSI for mild male factor and/or egg factor infertility, who have day three FSH values greater than 14 IU/ml inhibin B levels less than 16 and estradiol levels greater than 80 pg/ml, five or fewer eggs retrieved after COH with high dose (at least FSH 450 IU/day) gonadotropin dosing, and known diagnosis of female infertility.

Once control and dysfunctional oocytes and/or polar bodies are obtained, the telomeres from the oocytes and polar bodies are quantitatively analyzed to determine their average telomere length. Telomere length of control oocytes and polar bodies is quantitatively analyzed through Q-FISH analysis, as described in the materials and methods section and example III.

Example III

Analysis of Telomere Length Using Quantitative Fluorescence In Situ Hybridization (Q-FISH)

Q-FISH analysis is used to determine the telomere length of chromosomes from oocytes. Oocytes are obtained from a patient who is interested in determining the risk of aneuploidy in her oocytes. From the batch of oocytes obtained from the ova, a spare oocyte or oocytes are taken for Q-FISH analysis. Results obtained for spare oocytes are representative of the population of oocytes in the batch. Control oocytes are obtained from a woman with demonstrated fertility and are prepared according to the methods described in the materials and methods section and Example I. Control oocytes are analyzed prior to Q-FISH analysis of the oocyte of interest or, alternatively, are prepared for Q-FISH analysis alongside the experimental spare oocyte(s). Average telomere length from control oocytes is the standardized control to which the spare oocytes are compared. Chromosomal spreads are prepared by hypotonic treatment of oocytes with 1% sodium citrate for 20 min, followed by fixation in methanol:acetic acid (3:1). Chromosomal spreads are then allowed to air dry.

Fluorescence in situ hybridization (FISH) is performed according to the manufacturer's protocol with FITC-labeled peptide nucleic acid (PNA) probe (Applied Biosystems, Framingham, M) comprising the sequence CCCTAAC-CCTAACCCTAA (SEQ ID NO: 1). The telomere specific probe is hybridized under stringent conditions to the chromosomal spreads. Chromosomes are then counterstained with Hoechst 33342 at a concentration of 0.2 µg/ml. Chromosomes are mounted onto a glass slide in Vectashield mounting medium (Vector Laboratories, Burlingame, Calif.), and analyzed using fluorescence microscopy.

Telomere length is determined by quantitative digital microscopy and integrated optical density of the fluorescence signal. The signal from the FITC-labeled probe hybridized to the telomeres is detected using a Zeiss fluorescence microscope (Axiophot) with a FITC filter. Images of fluorescing telomeres are captured using an AxioCam digital microscope camera using AxioVision 2.0 software, Commercially available software, including MetaMorph (Universal Imaging Corporation™ Downingtown Pa.), is used to integrate the fluorescent intensity and area. The digital images are then used for quantitative analysis of telomere length based on criteria described in Zijlmans et al. (1997). Background is subtracted and integrated fluorescence intensity in individual telomeres of chromosome spreads is measured to indicate the length of telomeres (Zijlmans et al., 1997; Romanov, et al. Nature. 409:633-637 (2001)). The intensity of the fluorescence from each telomere is expressed in "Telomere Fluorescence Units" or "TFUs" and plotted on a graph for comparative purposes. Determined telomere lengths of the spare oocytes are compared to the results obtained for the control oocytes to establish whether the spare oocyte telomere lengths are abnormal. If the determined length of the oocyte's telomeres is found to be abnormal in comparison to the control or standardized average length, the batch of oocytes is considered at risk for aneuploidy and not fertilized for IVF purposes. If, however, the telomere length of the spare oocytes is found to be comparable to the control, the population of oocytes is not considered at risk for aneuploidy and is used for IVF procedures. Telomere lengths are determined by the number of tandem repeats of a specific nucleotide sequence found within the telomeres at the end of chromosomes. In humans and other vertebrates, the telomere repeats are commonly tandem repeats of the sequence TTAGGG.

One of ordinary skill in the art will recognize that the above-mentioned procedure for determining telomere length by Q-FISH analysis, can be repeated for a polar body or polar bodies which are obtained from fertilized or unfertilized oocytes. Polar bodies are obtained through conventional methods known to one of ordinary skill in the art.

Example IV

Comparative Study of Age and Telomere Length In Unfertilized Eggs

To show that telomere length is a predictor of the outcome of IVF and embryo transfer procedures, telomere length was determined in women of various ages who were undergoing IVF. Unfertilized human eggs (n=43) were obtained from consenting donors who had undergone IVF treatment. Clinical characteristics and outcomes were also obtained from patients' charts. Telomere lengths from the unfertilized eggs were measured by Q-FISH analysis. Telomere length was then compared with pregnancy outcome and analyzed by t test or logistic regression.

The results show that telomere maximum (19.3±3.1 kb. vs. 13.9±3.28 k.b., p<0.01) and mean (7.5±1.17 kb. vs. 6.2±1.69 k.b,) lengths were significantly longer and standard deviation greater (4.4±0.96 vs. 3.5±1.12) in eggs from patients who went on to become pregnant, compared to those who failed attempts at pregnancy. Minimum telomere length and number of missing telomere signals did not differ between groups. In addition, clinical predictors of fertility, including patients' age, baseline follicle stimulating hormone (FSH) level, egg number, body mass index, ovarian stimulation protocol, numbers of previous IVF cycles, diagnosis, or embryo morphology did not differ significantly between groups with these sample sizes.

In sum, increased egg telomere length predicts favorable reproductive outcome in infertile women undergoing IVF. Telomere length provided a better predictor of pregnancy outcome following IVF than patient age itself or other clinical parameters, including when telomere length was measured only in spare eggs.

Example V

Analysis of Telomere Length in Oocyte for In Vitro Fertilization

Upon obtaining a population of spare oocytes, Q-FISH analysis is performed, as described above in the materials and methods section and Example III, to determine the length of the oocyte's telomeres. The length of telomeres within the population is assumed to be similar, therefore allowing the ordinarily skilled artisan to determine whether the population of oocytes might be at risk for aneuploidy.

Example VI

Analysis of Telomere Length in Polar Body Prior to Implantation in a Subject

Upon obtaining the polar body from an oocyte, Q-FISH analysis is performed, as described above in the materials and methods section and Example III, to determine telomere length of the polar body. Determining the telomere length allows the ordinarily skilled artisan to assess the risk of aneuploidy, and subsequently whether the oocyte is likely to give rise to an abnormal embryo.

Example VII

Detection of TTAGGG Repeats at Chromosome Telomeric Ends

To detect the presence of TTAGGG repeats at the chromosome ends, the number of repeats comprising the telomeric ends determine the length of the telomeres, telomeric FISH was performed on oocyte metaphase spreads using a fluorescent FITC-labeled (CCCTAA)3 (SEQ ID NO: 10) peptide nucleic acid (PNA) probe, which is able to detect 200 bp of TTAGGG repeats at the telomeres. FISH was employed to measure telomere length in chromosomes spread from spare eggs matured from the GV stage after aspiration from consenting subjects undergoing ART and ICSI (FIG. 1)

Forty-three eggs were donated from 21 women, with 23 eggs coming from pregnant cycles and 20 from non-pregnant cycles. 10 (47.6%) of the women became pregnant and 11 (52.4%) did not. The clinical characteristics of these patients did not differ significantly between the pregnant and non-pregnant groups at the sample size studied (Table 1). The embryo morphology score was slightly worse in the non-pregnant group (p<0.04), although after correction for multiple comparisons this difference was only marginally significant.

TABLE 1

Clinical Characteristics and Pregnancy Outcomes:

| Variable (mean ± SD) | Pregnant (n = 10 women) | Not Pregnant (n = 20 women) | P-Value |
|---|---|---|---|
| Age | 34.2 ± 5.45 | 35.5 ± 3.24 | 0.52 |
| No. Oocytes | 15 ± 7.96 | 17.4 ± 12.96 | 0.61 |
| No. Cleaved (d.2) | 8.3 ± 5.2 | 4.5 ± 5.8 | 0.14 |
| No. Frozen | 3.9 ± 3.2 | 2.3 ± 4.7 | 0.37 |
| Embryo Morphology | 7.4 ± 1.22 | 6.2 ± 0.84 | 0.04 |
| Pt. BMI | 28.1 ± 4.17 | 28.4 ± 8.19 | 0.11 |
| D. 3 FSH | 6.5 ± 1.79 | 7.2 ± 3.25 | 0.56 |
| Diagnosis | | | 0.3 |
| Cycle No. | | | 0.44 |

Telomere lengths were normally distributed. Although clinical characteristics did not distinguish the pregnant vs. the non-pregnant group, nearly all measures of telomere length did differ significantly between the pregnant and non-pregnant groups (t-test) (Table 2). Mean and maximum telomere lengths were greater in oocytes from women who became pregnant compared to those who did not become pregnant. Variation in telomere length, measured by standard deviation, also was significantly greater in oocytes from women who became pregnant compared to those who did not (F test). No women became pregnant in this study who bad a mean telomere length in any spare oocytes less than 6.32 k.b. Minimum telomere length did not differ between groups, presumably because Q-FISH is not as accurate a measure of telomere length in the very short range compared to measurement of longer telomeres.

TABLE 2

Tetomere Length Metrics and Pregnancy Outcomes:

| Variable (mean ± SD) | Pregnant (n = 23) | Not Pregnant (n = 20) | P-Value |
|---|---|---|---|
| Mean Length (k.b) | 7.5 ± 1.17 | 6.2 ± 1.69 | 0.01 |
| Max. Length (k.b) | 19.3 ± 3.1 | 13.9 ± 3.28 | 0.01 |
| Variation (S.D.) | 4.4 ± 0.96 | 3.5 ± 1.12 | 0.01 |
| Min. Length (k.b.) | 0.87 ± .87 | 0.93 ± 0.74 | 0.89 |

Figure 2:
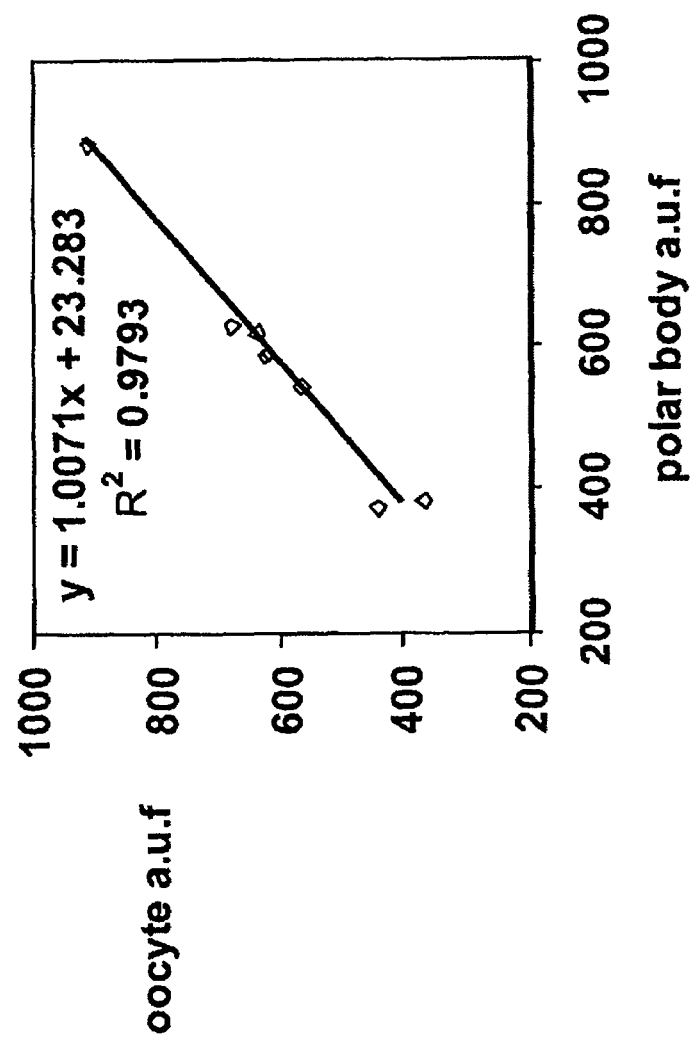
FIG. 2 is a plot showing telomere lengths were highly correlated between eggs and polar bodies.

Telomere lengths were highly correlated between polar bodies and oocytes (n=8; R2=97.8%) (FIG. 2). Thus, telomere length measured in the polar body should provide a highly accurate estimate of telomere lengths in embryos later transferred to patients.

INCORPORATION BY REFERENCE

The contents of all references, patents and published patent applications cited throughout this application, as well as the figures and the sequence listing, are incorporated herein by reference.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

The invention claimed is:

1. A method of in vitro fertilization comprising:
obtaining at least one chromosome from the polar body of a fertilized human oocyte;
measuring telomere length of the at least one chromosome;
selecting a fertilized human oocyte having a polar body for with the measured telomere length is 7.5 kb ±1.17 kb; and
after a period of incubation, implanting the embryo resulting from the selected fertilized human oocyte in a human subject.

2. A method for optimizing the viability of a human embryo comprising:
obtaining at least one chromosome from the polar body of a fertilized human oocyte;
measuring telomere length of the at least one chromosome;
selecting a fertilized human oocyte having a polar body for which the measured telomere length is 7.5 kb ±1.17 kb; and
after a period of incubation, implanting the embryo resulting from the selected fertilized human oocyte in a human subject.

* * * * *

UNITED STATES PATENT AND TRADEMARK OFFICE
CERTIFICATE OF CORRECTION

PATENT NO.        : 8,771,941 B2
APPLICATION NO.   : 12/482176
DATED             : July 8, 2014
INVENTOR(S)       : David L. Keefe It is certified that error appears in the above-identified patent and that said Letters Patent is hereby corrected as shown below:

In The Claims

At column 27, claim number 1, line number 38, please change the word "with", to the word "which".

Signed and Sealed this
Thirteenth Day of January, 2015

Michelle K. Lee
*Deputy Director of the United States Patent and Trademark Office*